US010234002B2

(12) United States Patent
Asselin et al.

(10) Patent No.: US 10,234,002 B2
(45) Date of Patent: *Mar. 19, 2019

(54) DEFLECTION MECHANISM

(71) Applicant: Boston Scientific Scimed, Inc., Maple Grove, MN (US)

(72) Inventors: William Asselin, Lunenburg, MA (US); Michael Barenboym, Bedford, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/491,535

(22) Filed: Apr. 19, 2017

(65) Prior Publication Data
US 2017/0268639 A1    Sep. 21, 2017

Related U.S. Application Data

(63) Continuation of application No. 14/199,287, filed on Mar. 6, 2014, now Pat. No. 9,657,817.
(Continued)

(51) Int. Cl.
*A61B 1/00* (2006.01)
*F16H 21/40* (2006.01)
(Continued)

(52) U.S. Cl.
CPC .......... *F16H 21/40* (2013.01); *A61B 1/0052* (2013.01); *A61M 25/0136* (2013.01);
(Continued)

(58) Field of Classification Search
USPC ................................................ 600/146–149
See application file for complete search history.

(56) References Cited

U.S. PATENT DOCUMENTS 2,453,862 A    11/1948    Salisbury
4,499,895 A     2/1985    Takayama
(Continued)

FOREIGN PATENT DOCUMENTS

EP    2 343 024 A2     7/2011
EP    2 532 297 A1    12/2012

OTHER PUBLICATIONS

Allemann, P. et al., "Joystick Interfaces Are Not Suitable for Robotized Endoscope Applied to NOTES," Surg. Innov., Jun. 2009; 16(2); 1 page (Abstract).
(Continued)

*Primary Examiner* — Matthew J Kasztejna
(74) *Attorney, Agent, or Firm* — Bookoff McAndrews, PLLC

(57) ABSTRACT

A steering mechanism may comprise an actuation system for one-fingered operation by a user, the system configured to move at least a distal portion of the medical device such that 360 degree articulation is achievable, and a housing coupled to the system, the housing having proximal and distal ends. The system may comprise a first lever rotatable about a first axis, the first lever coupled to a first cam and configured to move the first cam from a first position to a second position when rotated about the first axis to deflect the distal portion; and a second lever rotatable about a second axis, the second lever coupled to a second cam and configured to move the second cam from a first position to a second position when rotated about the second axis to deflect the distal portion, wherein the first lever is coupled to the second lever.

20 Claims, 7 Drawing Sheets

Related U.S. Application Data

(60) Provisional application No. 61/776,152, filed on Mar. 11, 2013.

(51) Int. Cl.
*A61B 1/005* (2006.01)
*A61M 25/01* (2006.01)
*A61B 17/00* (2006.01)

(52) U.S. Cl.
CPC ....... *A61M 25/0147* (2013.01); *A61B 1/0057* (2013.01); *A61B 2017/003* (2013.01); *Y10T 74/18568* (2015.01)

(56) References Cited

U.S. PATENT DOCUMENTS

| | | | |
|---|---|---|---|
| 4,503,842 A | 3/1985 | Takayama | |
| 4,620,176 A | 10/1986 | Hayes | |
| 4,721,099 A | 1/1988 | Chikama | |
| 5,325,845 A * | 7/1994 | Adair | A61B 1/0055 600/114 |
| 5,347,989 A | 9/1994 | Monroe et al. | |
| 5,589,854 A | 12/1996 | Tsai | |
| 5,846,183 A | 12/1998 | Chilcoat | |
| 6,123,699 A | 9/2000 | Webster, Jr. | |
| 7,285,117 B2 | 10/2007 | Krueger et al. | |
| 7,615,067 B2 | 11/2009 | Lee et al. | |
| 7,682,358 B2 | 3/2010 | Gullickson et al. | |
| 8,012,100 B2 | 9/2011 | Ward | |
| 8,048,024 B2 | 11/2011 | Tah et al. | |
| 8,048,025 B2 | 11/2011 | Barenboym et al. | |
| 8,177,710 B1 | 5/2012 | Hosaka et al. | |
| 8,287,449 B2 | 10/2012 | Tanaka | |
| 8,790,250 B2 | 7/2014 | Petersen et al. | |
| 8,834,357 B2 | 9/2014 | Oskin et al. | |
| 9,101,735 B2 | 8/2015 | Rothe et al. | |
| 2004/0059191 A1 | 3/2004 | Krupa et al. | |
| 2004/0193016 A1 | 9/2004 | Root et al. | |
| 2007/0282167 A1 | 12/2007 | Barenboym et al. | |
| 2008/0287862 A1 | 11/2008 | Weitzner et al. | |
| 2009/0234280 A1 | 9/2009 | Tah et al. | |
| 2010/0004591 A1 | 1/2010 | Barenboym et al. | |
| 2010/0121147 A1 | 5/2010 | Oskin et al. | |

OTHER PUBLICATIONS

International Search Report and Written Opinion for counterpart PCT Application No. PCT/US2014/021234 dated Jul. 23, 2014 (11 pages).

* cited by examiner

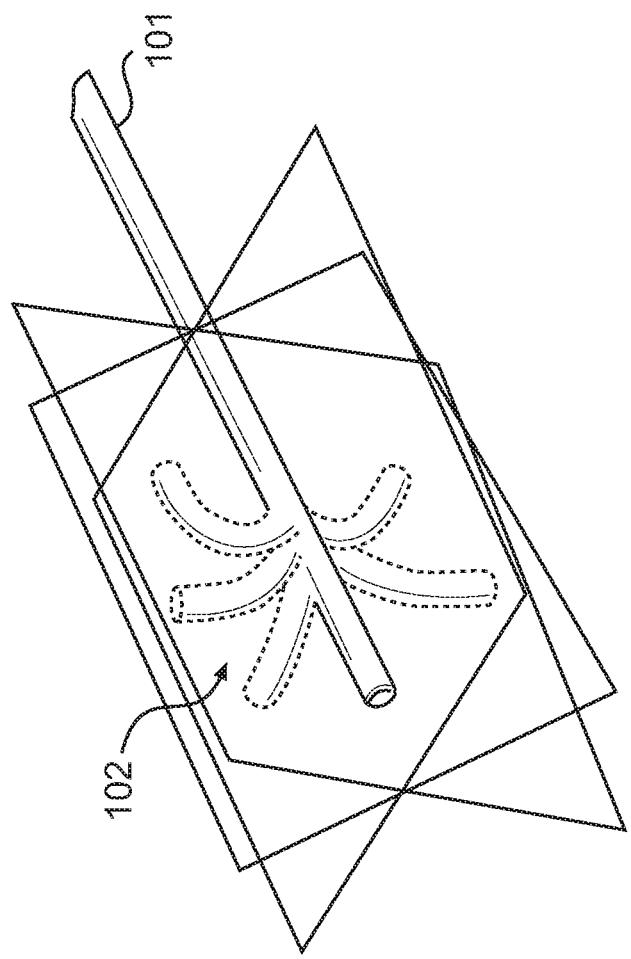

DEFLECTION MECHANISM

CROSS-REFERENCE TO RELATED APPLICATION

This application is a continuation application of U.S. patent application Ser. No. 14/199,287, filed Mar. 6, 2014, which claims the benefit of U.S. Provisional Application No. 61/776,152, filed Mar. 11, 2013, the disclosure of each of which is incorporated herein by reference in its entirety.

TECHNICAL FIELD

The present disclosure generally relates to a mechanism for controlling articulation of a steerable portion of a medical device.

BACKGROUND

Steering mechanisms are used to steer or direct a medical instrument, for example a catheter or endoscope, to a desired position or location in a body of a patient. Known steering mechanisms may present certain drawbacks for users. One known steering mechanism, for example, resembles a joystick. The configuration of the joystick usually includes a plate attached to control wires. The plate, however, must be large to accommodate the desired articulations of the steerable medical device. Additionally, the single control element encompassed in the joystick control mechanism makes the introduction of force leverage difficult, especially in a procedure during which an increased leverage is needed for different articulation planes.

Another known steering mechanism includes multiple slidable buttons. Each button is connected to a puller wire so that when the button is moved, the puller wire moves the catheter in a single direction associated with the puller wire. Thus, at least four slidable buttons are required to achieve 360 degree articulation of the catheter or endoscope. The sliding motion of the buttons on this steering mechanism makes introduction of force leverage very difficult.

The present disclosure provides mechanisms that avoid or otherwise address one or more drawbacks associated with known steering mechanisms.

SUMMARY OF THE DISCLOSURE

The present disclosure is drawn to a steering mechanism for use in a medical device, comprising: a first lever rotatable about a first axis, the first lever coupled to a first cam and configured to move the first cam from a first position to a second position when rotated about the first axis to deflect the distal portion; a second lever rotatable about a second axis, the second lever coupled to a second cam and configured to move the second cam from a first position to a second position when rotated about the second axis to deflect the distal portion, wherein the first lever is coupled to the second lever; and a housing coupled to the first lever and the second lever, the housing having a proximal end and a distal end.

Embodiments of the steering mechanism may include one or more of the following features: an object connecting the first lever to the second lever; wherein the first lever includes a first slot, the object configured to slide within the first slot to cause the second lever to rotate about the second axis; wherein the second lever includes a second slot, the object configured to slide within the second slot to cause the first lever to rotate about the first axis, wherein the first lever is configured to move independently of the second lever and the second lever is configured to move independently of the first lever; wherein moving only the first lever or only the second lever allows for deflection of the distal portion of the medical device along one plane; wherein the first lever and the second lever are configured to move simultaneously; wherein the first lever includes a first slot and the second lever includes a second slot, and the object is configured to slide within the first slot and the second slot simultaneously to deflect the distal portion of the medical device along more than two planes; wherein the first lever has a first end coupled to the housing at a pivot and a second free end; an arm coupled to the second lever, the arm adapted to engage a portion of the second cam as the second lever is rotated about the second axis, the arm including a protrusion that extends at least partially through an opening formed on the second cam; and wherein the first lever is curved to match a curvature of the proximal end of the housing.

The present disclosure is further drawn to a steering mechanism for use in a medical device, comprising: a first lever including a first slot and coupled to a first cam; a second lever including a second slot and coupled to a second cam; and an object connecting the first lever to the second lever through the first slot and the second slot; wherein the first lever is rotatable about a first axis, the first lever configured to move the first cam from a first position to a second position when rotated about the first axis, and the second lever is rotatable about a second axis, the second lever configured to move the second cam from a first position to a second position when rotated about the second axis. In some embodiments, sliding the object within the first slot causes the second lever to rotate about the second axis, and sliding the object within the second slot causes the first lever to rotate about the first axis.

The present disclosure is further drawn to a steering mechanism for use in a medical device, comprising: a first lever rotatable about a first axis, the first lever coupled to a first cam and configured to move the first cam from a first position to a second position when rotated about the first axis to provide a first deflection of a distal end of the medical device; a second lever rotatable about a second axis, the second lever coupled to a second cam and configured to move the second cam from a first position to a second position when rotated about the second axis to provide a second deflection of the distal end of the medical device, and an object connecting the first lever to the second lever, wherein the first lever and the second lever are configured to move independently or concertedly by moving the object. In some embodiments, the object includes a button slidable within a first closed slot in the first lever and a second closed slot in the second lever. In some embodiments, sliding the button within the first closed slot and the second closed slot simultaneously allows for deflection of the distal end of the medical device along more than two planes.

BRIEF DESCRIPTION OF THE FIGURES

FIGS. 5A-5D illustrate deflection of a steerable member of the device of FIG. 1 according to the present disclosure.

DETAILED DESCRIPTION

Devices for controlled articulation of a steerable member are described herein. In some embodiments, for example, the device may comprise a steering mechanism. The steering mechanism can be used as part of, or in conjunction with, a medical device including a steerable member, such as, for example, a catheter or endoscope. The steerable member may be useful in various medical procedures, such as navigating pathways in a body of a patient.

Figure 1:
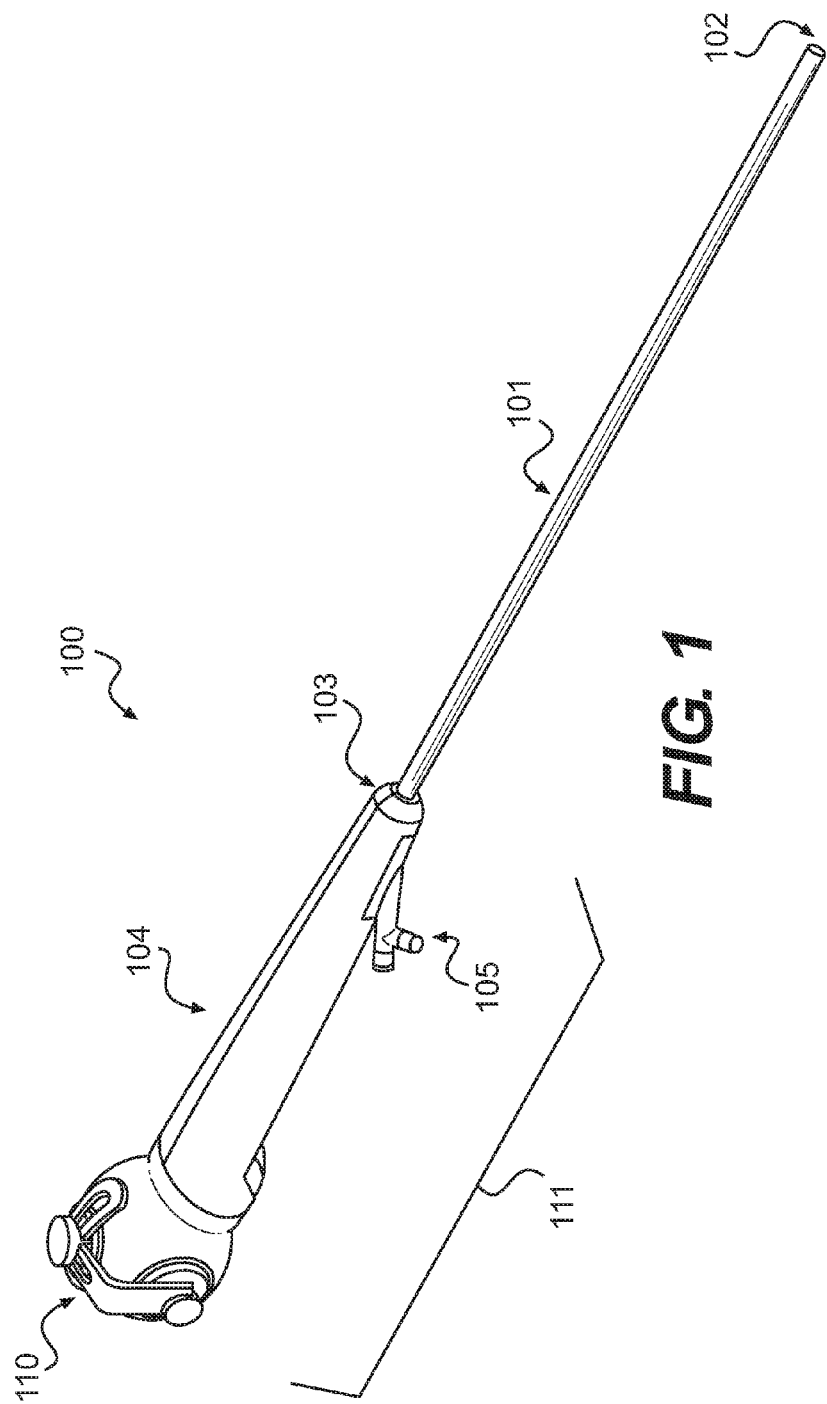
FIG. 1 shows a device including a steering mechanism according to the present disclosure.

In one embodiment of the present disclosure, schematically illustrated in FIG. 1, the device 100 may comprise steering mechanism 111 and elongate member 101. The steering mechanism includes an actuation system 110 and a housing 104 equipped with one or more ports 105. The elongate member 101 includes a proximal end 103 and a distal end 102. In some embodiments, the actuation system 110 is adapted to control articulation of the distal end 102 of the elongate member 101 along a first plane and a second plane different than the first plane. In some embodiments, for example, the steering mechanism 111 is adapted to move the distal end of the elongate member along the first plane and the second plane such that 360 degree articulation of the device is achievable. See, e.g., FIGS. 5A-5D, discussed further below.

The actuation system 110 may be adapted for one-handed operation by a user. In some embodiments, for example, the actuation system 110 is adapted for one-fingered operation. The user may hold or lay the housing 104 of the steering mechanism 111 in his/her hand and manipulate the actuation system 110 with a thumb or finger of the same hand.

Figure 2:
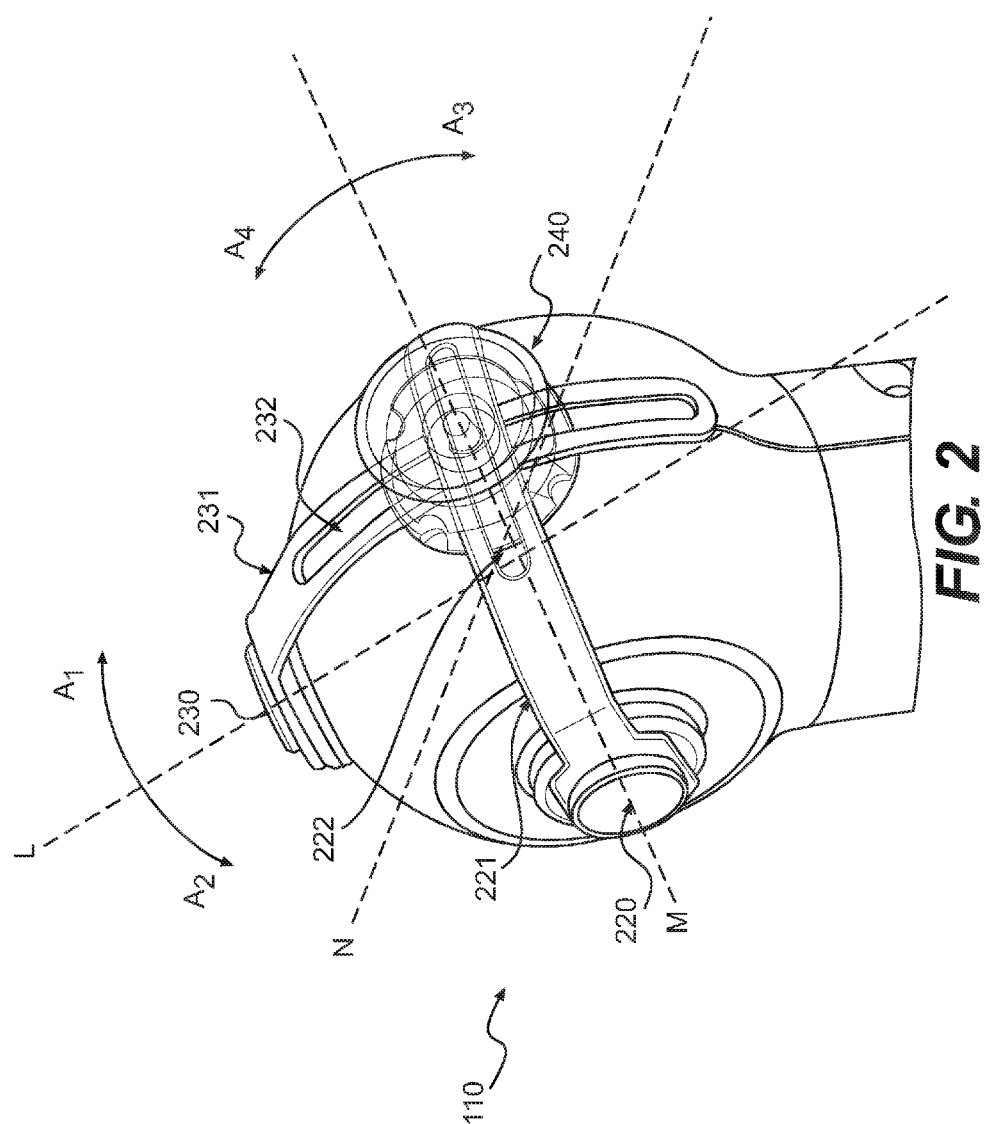
FIG. 2 shows an actuation system of the device of FIG. 1, including first and second levers according to the present disclosure.

An embodiment of the actuation system 110 is shown in FIG. 2, comprising a first lever 221 and a second lever 231. The first lever 221 is fixedly coupled to a proximal end of the housing 104 at a first pivot 220 and rotatable, e.g., in directions $A_3$ and $A_4$ about axis M. Second lever 231 is fixedly coupled to the proximal end of the housing 104 at a second pivot 230 and rotatable, e.g., in directions $A_1$ and $A_2$ about axis L. The first lever 221 and/or the second lever 231 may have one end of the lever attached to the housing 104 and an opposite free end. In FIG. 2, for example, the first lever 221 has a first end coupled to the housing 104 at the first pivot 220 and a second free end. Similarly, the second lever 231 has a first end coupled to the housing 104 at the second pivot 230 and an opposite free end.

Further referring to FIG. 2, each of the first lever 221 and second lever 231 includes a slot, e.g., first slot 222 and second slot 232, respectively, extending along at least a portion of the length of each lever. The first and second levers are coupled together via object 240 disposed and slidable within the first and second slots. The slots may be closed as shown in FIG. 2. In some embodiments, the object 240 may comprise a button configured to slide within the first slot 222 and second slot 232 as shown in FIG. 2. Such a button may have any suitable dimensions, geometry, and/or surface design (e.g., convex or concave) to be useful in single handed operation, including, for example, a generally cylindrical shape. Other suitable means of coupling the first lever to the second lever, e.g., an object of another form or shape may also be used according to the present disclosure.

The object 240 may be moved within the first slot 222 to rotate the second lever 231 (e.g., about the second axis L). Similarly, the object 240 may be moved within the second slot 232 to rotate the first lever 221 (e.g., about the first axis M). In addition, the object 240 may be moved within both slots simultaneously to rotate both the first and second levers. Thus, a user may manipulate the actuation system 110 with a single finger, e.g., the thumb or other finger, by moving the object 240 so as to rotate the first lever 221 and/or second lever 231.

In some embodiments, the housing 104 may be contoured to fit the hand of a user to facilitate operation of the actuation system 110. The proximal end of the housing 104 may take any form suitable for operation of the actuation system 110 as described herein. In some embodiments, for example, the proximal end of the housing has a curvature, e.g., a spherical shape. The first pivot 220 and the second pivot 230 may have substantially the same lateral position but different longitudinal positions as shown in FIGS. 1 and 2. The first pivot and second pivot may also be located at different lateral and longitudinal positions. In some embodiments, the first and second levers are curved to match the spherical shape of the proximal end of the housing 104. The object 240 may, for example, slide within the first slot 222 and/or the second slot 232 of levers 221 and 231, respectively, on the outside of the spherical proximal end of the housing 104.

Figure 3:
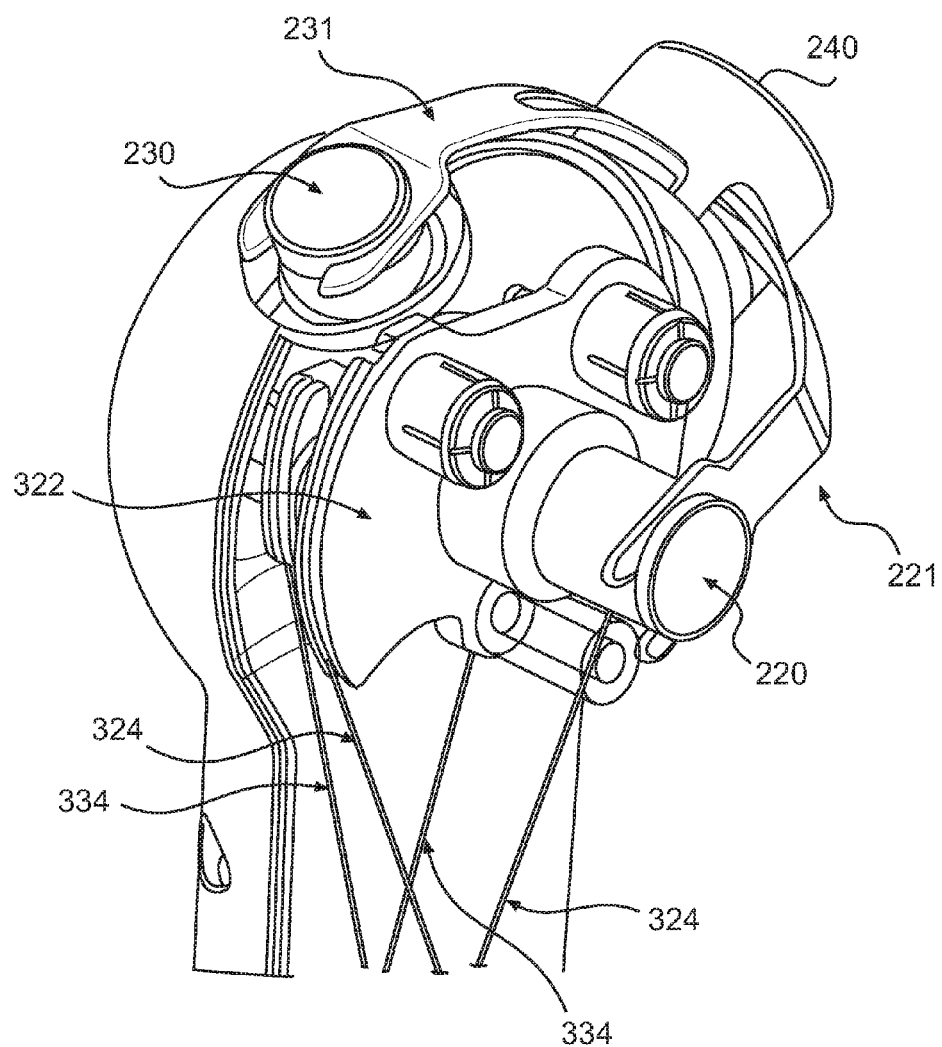
FIG. 3 shows a portion of a steering mechanism of the device of FIG. 1, including a first cam according to the present disclosure.
Figure 4:
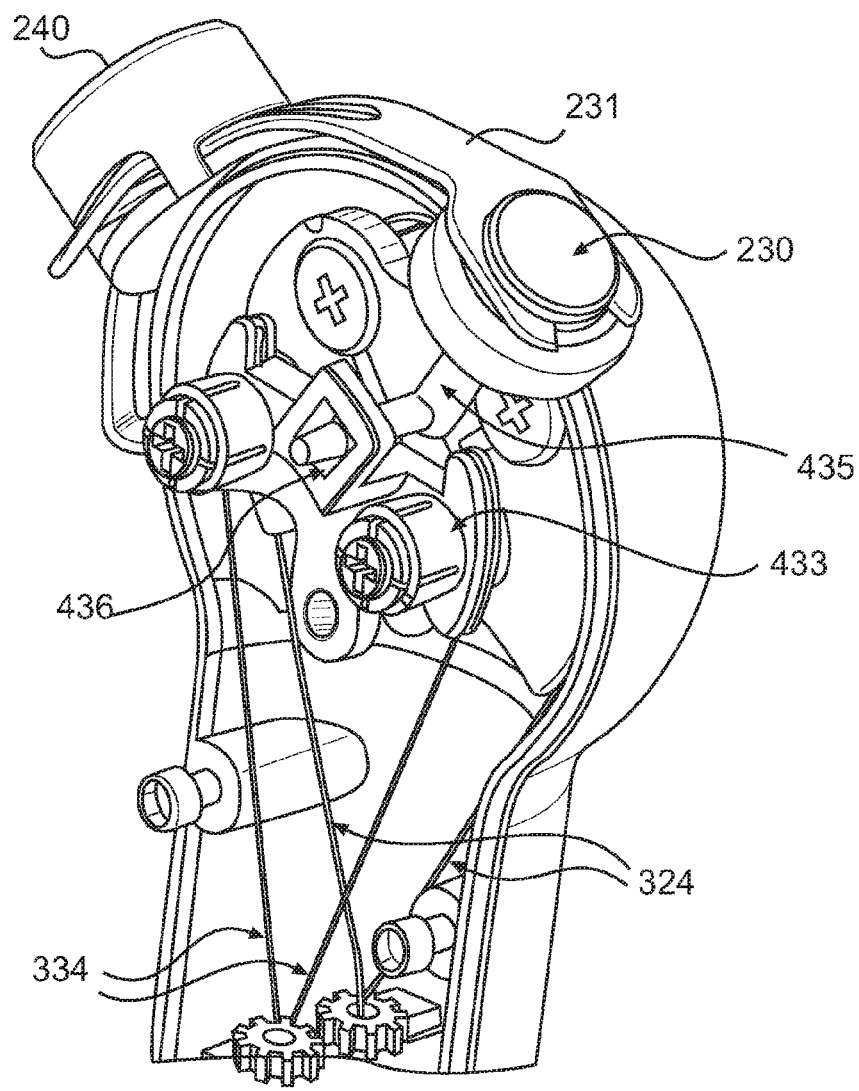
FIG. 4 shows another portion of a steering mechanism of the device of FIG. 1, including a second cam according to the present disclosure.

FIGS. 3 and 4 show views of an actuation system according to the present disclosure with portions of a housing 104 of the actuation system 110 removed, revealing a first cam 322 coupled to the first lever 221 (FIG. 3) and a second cam 433 coupled to the second lever 231 (FIG. 4). Referring to FIG. 3, the first lever 221 is coupled to first cam 322, which in turn is coupled to steering wires 324 that are fixed at the distal end 102 of the device 100. Rotation of the first lever 221 at the first pivot 220 (e.g., about the first axis M) directly rotates first cam 322, thus moving steering wires 324 to cause deflection of the distal end portion 102 of the device 100 (FIG. 1) along a first plane. See, e.g., FIG. 5A, discussed below.

Referring now to FIG. 4, the second lever 231 is coupled to an arm 435 including a protrusion, e.g., a pin or other element, which engages the second cam 433 through an opening 436 formed on the second cam 433. The second cam 433 is coupled to steering wires 334 that are fixed at the distal end 102 of the device 100. Rotation of the second lever 231 at the second pivot 230 causes the arm 435 to rotate and engage the second cam 433 with the protrusion by contacting an inside surface of the opening 436. Rotation of the second cam 433 moves steering wires 334 to cause deflection of the distal end portion 102 of the device 100 (FIG. 1) along a second plane different from the first plane. See, e.g., FIG. 5B, discussed below. Other suitable mechanisms by which the second lever may engage the second cam are also contemplated consistent with the present disclosure.

In some embodiments of the present disclosure, the first cam 322 and the second cam 433 are parallel to one another, and are adjacent to each other.

Figure 5A:
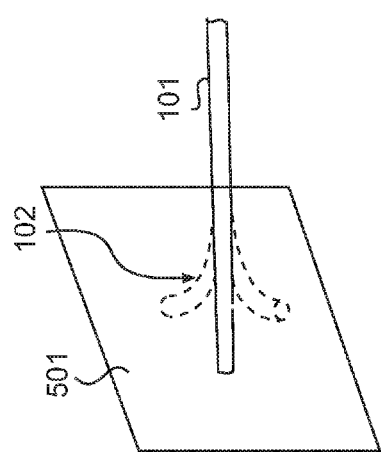
Figure 5A:
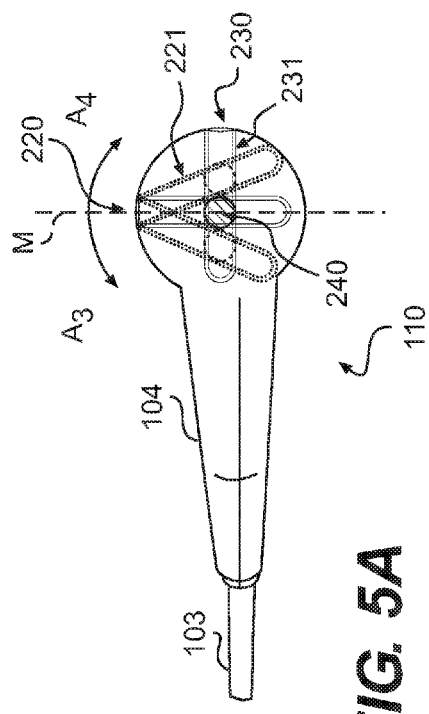
Figure 5B:
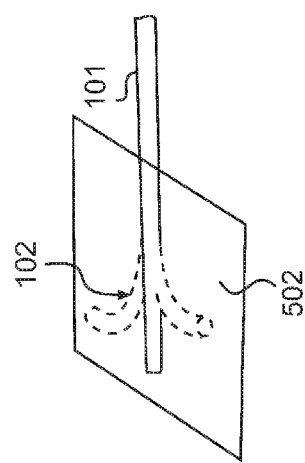
Figure 5B:
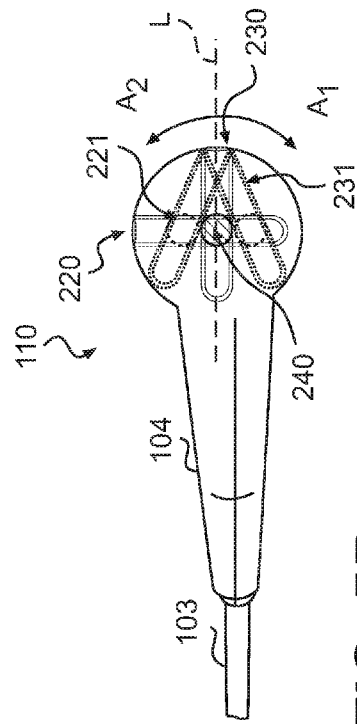
Figure 5C:
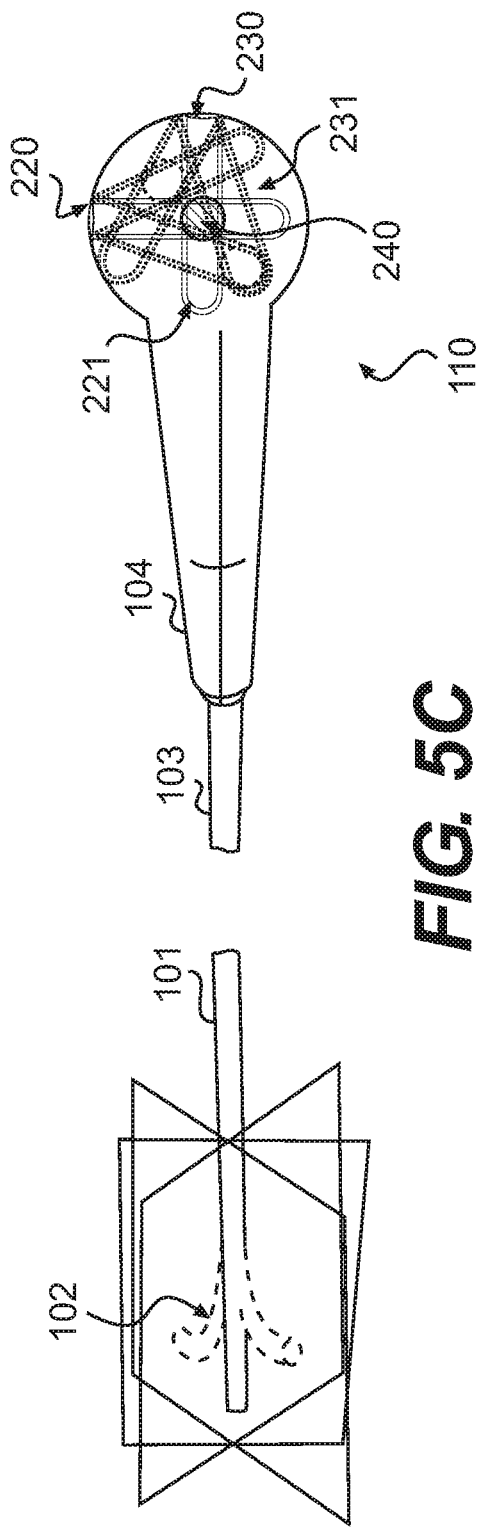

As illustrated in FIGS. 5A-5C, the object 240 coupled to the first lever 221 and the second lever 231 can be moved to cause deflection of the distal end 102 of the elongate member 101. As shown in FIG. 5A, moving the object 240 within the slot defined by the second lever 231 so that the second lever 231 remains stationary causes rotation of the first lever 221 and the first pivot 220 about axis M in directions $A_3$ and/or $A_4$ (indicated by the dotted line representations to the left and right of the first lever 221). Rotation of the first lever 221 accordingly causes deflection of the distal end 102 of the device 100 along a first plane 501.

Similarly, as shown in FIG. 5B, moving the object 240 within the slot defined by the first lever 221 so that the first lever remains stationary causes rotation of the second lever 231 and the second pivot 230 about axis L in directions $A_1$ and/or $A_2$ (indicated by the dotted line representations above and below second lever 231). Rotation of the second lever causes deflection of the distal end 102 of the device 100 along a second plane 502 different from the first plane 501. Thus, in some embodiments, each of the first lever 221 and second lever 231 may be rotated independently of each other such that each of the first cam 322 and second cam 433 may be manipulated independently.

The first lever 221 and the second lever 231 may be rotated simultaneously as shown in FIG. 5C. The object 240 may be moved within both the first slot and the second slot defined by the first lever 221 and the second lever 231, respectively, thus rotating both levers simultaneously. In such embodiments, the object 240 may be moved in order to engage both the first cam 322 and the second cam 433. As shown in FIG. 5C, rotation of both levers causes deflection of the distal end 102 of the device 100 along one or more planes other that the first plane 501 and second plane 502 discussed above with respect to rotating each lever independently. In some embodiments, for example, moving the object 240 to rotate both the first and second levers allows for deflection of the distal end along two or more planes, such as a plurality of planes, to achieve 360 degree articulation as illustrated in FIG. 5D.

In some embodiments of the present disclosure, the first lever 221 and the second lever 231 may be biased toward a starting or neutral position before rotation as shown, for example, in FIG. 2. In the starting position, the first lever 221 and the second lever 231 may be positioned substantially orthogonal to each other. In some embodiments, the first lever and/or second lever may include a locking mechanism, e.g., to maintain the distal end in a particular configuration. The locking mechanism may, for example, be actuated to prevent the object from moving within the slot defined by the first lever, second lever, or both the first lever and second lever, or alternatively may be actuated to allow movement of the lever(s).

Further, for example, some embodiments may allow one lever to be held in place while the other lever is operated. In some embodiments, movement of one or both of the first and second levers may be restricted by a friction hold or a ratcheting hold, wherein moving the lever(s) requires a force to overcome the hold. In some embodiments, one or both of the slots may have, for example, a friction or ratcheting connection to the object. In some embodiments, surface contact between the underside of the levers and the housing may have, for example, a friction hold or a ratcheting hold.

In some embodiments of the present disclosure, the housing 104 of the device 100 may include one or more ports 105 as shown in FIG. 1. The one or more ports 105 may be adapted to be connected to one or more working channels or lumens extending through at least a portion of the elongate member 101 towards the distal end 102 of the device 100. In some embodiments, the working channels may extend to or towards a treatment site in a body of a patient. The one or more ports 105 may be configured to receive medical instrumentation, or aspiration, irrigation, or other fluid conveyance. For example, in some embodiments, a port 105 may be configured to receive one or more of a guidewire, laser fiber, stone basket, biopsy device, or other medical instrumentation. The port 105 allows a user to insert the medical instrumentation into the working channel and through the elongate member 101 to the treatment site.

While various embodiments of the present disclosure have been described above, it should be understood that they have been presented by way of example only and are not limiting. Thus, the breadth and scope of the disclosure should not be limited by any of the above-described embodiments, but should be defined only in accordance with the claims and their equivalents.

What is claimed is:

1. A medical device, comprising:
a housing having a proximal portion and a distal portion, wherein at least a portion of the proximal portion of the housing includes a spherical portion;
a member coupled to the distal portion of the housing;
a first positioning element rotatable about a first axis and coupled to the spherical portion at a first location; and
a second positioning element rotatable about a second axis and coupled to the spherical portion at a second location,
wherein the first location and the second location are positioned approximately 90 degrees apart in a plane extending through the spherical portion, and wherein a portion of the first positioning element overlaps with a portion of the second positioning element.

2. The medical device of claim 1, wherein rotation of the first positioning element deflects a distal portion of the member in a first plane, and rotation of the second positioning element deflects the distal portion of the member in a second plane.

3. The medical device of claim 1, wherein the first positioning element is coupled to the second positioning element via an object, and
wherein the first positioning element and the second positioning element overlap over a portion of the spherical portion, and wherein the position of the overlap relative to the first location and the second location corresponds to a deflection of the distal end of the member.

4. The medical device of claim 3, wherein the object is slideable within a first slot in the first positioning element and within a second slot in the second positioning element.

5. The medical device of claim 4, wherein the first slot and the second slot are closed.

6. The medical device of claim 1, wherein at least one of the first positioning element or the second positioning element includes a free end that moves angularly over a portion of the spherical portion relative to either the first location or the second location.

7. The medical device of claim 1, wherein at least one of the first positioning element or the second positioning element conforms to a shape of the spherical portion.

8. The medical device of claim 1, wherein the first positioning element is coupled to a first cam and wherein rotation about the first axis causes the first cam to move from a first position to a second position, and wherein the movement of the first cam causes a distal portion of the member to deflect in a first plane; and
wherein the second positioning element is coupled to a second cam and wherein rotation about the second axis causes the second cam to move from a first position to a second position, and wherein the movement of the second cam causes the distal portion of the member to deflect in a second plane.

9. The medical device of claim 1, wherein the housing further includes at least one port, and
the at least port accesses an internal lumen that connects to a distal opening at a distal end of the member.

10. A steering mechanism for use in a medical device, comprising:
a housing having an interior and an exterior;

a first lever positioned exterior to a proximal portion of the housing and rotatable about a first axis to control a first cam;

a second lever positioned exterior to the proximal portion of the housing and rotatable about a second axis to control a second cam; and an object positioned exterior to the proximal portion of the housing and coupled to the first lever and the second lever via a first slot in the first lever and a second slot in the second lever, wherein the object is movable about at least a portion of the exterior of the proximal portion of the housing, and wherein movement of the object controls the pivoting of the first lever and the second lever.

11. The steering mechanism of claim 10, wherein the object is movable within the first slot of the first lever and within the second slot of the second lever.

12. The steering mechanism of claim 11, wherein the movable object includes a button, and wherein moving the button within the first slot of the first lever or the second slot of the second lever deflects a distal portion of the medical device.

13. The steering mechanism of claim 10, wherein the object is movable relative to each of the first lever and the second lever, and the object is not directly connected to the housing, and wherein the first lever and the second lever overlap over a portion of the proximal portion, and wherein the position of the overlap relative to the first axis and the second axis corresponds to a deflection of the distal end of the member.

14. A medical device, comprising:

a housing having a proximal portion and a distal portion, wherein at least a portion of the proximal portion of the housing includes an at least partially spherical end portion;

a member coupled to the housing and including a distal end;

a first lever rotatable about a first axis and coupled to the spherical end portion via a first pivot at a first location on the spherical end portion; and a second lever rotatable about a second axis and coupled to the spherical end portion via a second pivot at a second location on the spherical end portion, wherein the first lever and the second lever overlap over a portion of the spherical end portion, and wherein the position of the overlap relative to the first location and the second location corresponds to a deflection of the distal end of the member.

15. The medical device of claim 14, further including a movable object connecting the first lever and the second lever at the overlap of the first lever and the second lever.

16. The medical device of claim 15, wherein at least one of the first lever or the second lever includes an internal slot, and wherein the movable object is coupled to and movable relative to at least one of the first lever or the second lever within the internal slot.

17. The medical device of claim 16, wherein the movable object is configured to deflect the distal portion of the housing such that 360 degree articulation is possible.

18. The medical device of claim 14, wherein at least one of the first lever or the second lever includes a free end that moves angularly over a portion of the spherical end portion relative to the first pivot or the second pivot.

19. The medical device of claim 14, wherein the first lever is coupled to a first cam and wherein rotation of the first lever about the first axis causes the first cam to move from a first position to a second position, and wherein the movement of the first cam causes the distal end of the member to deflect in a first plane; and wherein the second lever is coupled to a second cam and wherein rotation of the second lever about the second axis causes the second cam to move from a first position to a second position, and wherein the movement of the second cam causes the distal end of the member to deflect in a second plane.

20. The medical device of claim 14, wherein the first location and the second location are positioned approximately 90 degrees apart in a plane through the at least partially spherical portion of the housing at different longitudinal positions.

* * * * *